United States Patent
Ten Kate et al.

(10) Patent No.: US 11,410,521 B2
(45) Date of Patent: Aug. 9, 2022

(54) FALL DETECTOR INCORPORATING PHYSIOLOGICAL SENSING

(71) Applicant: KONINKLIJKE PHILIPS N.V., Eindhoven (NL)

(72) Inventors: Warner Rudolph Theophile Ten Kate, Waalre (NL); Inge Theodora Margretha Geven, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/324,843

(22) Filed: May 19, 2021

(65) Prior Publication Data
US 2021/0366257 A1     Nov. 25, 2021

Related U.S. Application Data

(60) Provisional application No. 63/027,392, filed on May 20, 2020.

(51) Int. Cl.
*G08B 21/04*     (2006.01)
*G08B 21/18*     (2006.01)

(52) U.S. Cl.
CPC ....... *G08B 21/043* (2013.01); *G08B 21/0446* (2013.01); *G08B 21/0453* (2013.01); *G08B 21/182* (2013.01)

(58) Field of Classification Search
CPC .................................................. G08B 21/043
See application file for complete search history.

(56) References Cited

U.S. PATENT DOCUMENTS

| | | | |
|---|---|---|---|
| 8,552,871 B2 | 10/2013 | Park et al. | |
| 2013/0138395 A1* | 5/2013 | Baggen | A61B 5/7246 702/181 |
| 2014/0142460 A1* | 5/2014 | Zhang | A61B 5/1117 600/547 |
| 2016/0038061 A1 | 2/2016 | Kechichian et al. | |
| 2017/0238812 A1 | 8/2017 | Atlas | |

FOREIGN PATENT DOCUMENTS

| | | |
|---|---|---|
| CN | 108354610 A | 8/2018 |
| WO | 2012146957 A1 | 11/2012 |
| WO | 2019097248 A1 | 5/2019 |
| WO | 2020002175 A1 | 1/2020 |

OTHER PUBLICATIONS

He, X. et al., "Video-Based Analysis of Heart Rate Applied to Falls", 2018, IEEE Instrumentation and Measurement Society.
(Continued)

*Primary Examiner* — Travis R Hunnings

(57) ABSTRACT

A method for detecting a fall by a user wearing a fall detector, including: detecting a trigger event identifying the time location of a possible fall event in user data; extracting motion features from motion data and physiological features from physiological data from within a time window around the identified time location; and determining whether the detected trigger event is a fall by the user by inputting the at least one of the motion features and at least one of the physiological features into a classifier.

22 Claims, 3 Drawing Sheets

(56) References Cited

OTHER PUBLICATIONS

Melillo. P. et al., "Wearable technology and ECG processing for fall risk assessment, prevention and detection", 2015, IEEE.
Nocua, R. et al., "Evaluation of the autonomic nervous system for fall detection", 31st Annual International Conference of the IEEE EMBS, Minneapolis, Minnesota, USA, Sep. 2-6, 2009.
Shahiduzzaman, M., "Fall Detection by Accelerometer and Heart Rate Variability Measurement", Global Journal of Computer Science and Technology: G Interdisciplinary, 2015.
International Search Report and Written Opinion from PCT/EP2021/062392 dated Aug. 11, 2021.

* cited by examiner

FALL DETECTOR INCORPORATING PHYSIOLOGICAL SENSING

CROSS-REFERENCE TO PRIOR APPLICATIONS

This application claims the benefit of U.S. Provisional Application No. 63/027,392, filed on 20 May 2020. This application is hereby incorporated by reference herein.

TECHNICAL FIELD

Various exemplary embodiments disclosed herein relate generally to a system and method for detecting falls using physiological measurements such as for example heart rate and skin conductance sensing.

BACKGROUND

Wearable devices that host automatic fall detection usually make use of estimated values of height changes, impacts, and possibly orientation changes. Sensors that provide the signals to perform fall estimation include air pressure sensors, accelerometers, gyroscopes and magnetometers. Typically, the estimated feature values are combined in a classifier, which decides whether the event is a fall or a non-fall. The accuracy of the classifier depends on the distinguishing power of these feature values. The distinguishing power relates to the distribution of possible values that may happen during a fall and during non-fall events. The less the fall and non-fall distributions overlap, the better the accuracy. In general, at body torso locations these distributions are often sufficiently different between falls and non-fall events to realize high accuracy detection outcomes.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method for detecting a fall by a user wearing a fall detector, including: detecting a trigger event identifying the time location of a possible fall event in user data; extracting motion features from motion data and physiological features from physiological data from within a time window around the identified time location; and determining whether the detected trigger event is a fall by the user by inputting the at least one of the motion features and at least one of the physiological features into a classifier.

Various embodiments are described, wherein the motion data includes one of acceleration data, height data, angular velocity data, and acceleration data and height data.

Various embodiments are described, wherein the motion data includes data from an accelerometer.

Various embodiments are described, wherein the physiological data include one of heart rate data, skin conductance data, and heart rate and skin conductance data.

Various embodiments are described, wherein extracting motion features and physiological features further includes: determining a first physiological data value at a first time before the trigger event; determining a second physiological data value at the trigger event; determining a third physiological data value at a third time after the trigger event, wherein at least one physiological feature is based upon a difference between two of the first, second, and third physiological data values.

Various embodiments are described, wherein the physiological features are based upon a difference between the first and second physiological values, the second and third physiological values, the first and third physiological values, and second physiological value and one half the sum of the first and third physiological feature.

Various embodiments are described, wherein detecting an impact based upon motion data further includes determining that a change in acceleration over a specified time exceeds a threshold value.

Various embodiments are described, further including determining that extracted motion features are outside a specified normal range of values and then determining that the impact is not a fall by the user.

Various embodiments are described, further including when a fall is indicated, receiving an output from an exception machine learning classifier that indicates that the impact is not a fall.

Various embodiments are described, wherein the machine learning classifier includes: a motion classifier that determines whether the impact is a fall, a non-fall, or undetermined based upon the extracted motion features and a first threshold value and a second threshold value; and a physiological classifier that determines whether the impact is a fall or a non-fall based upon both the extracted motion features and the extracted physiological features when the output of the motion classifier is undetermined.

Various embodiments are described, further including receiving the physiological data from a remote sensor.

Further various embodiments relate to a fall detector for detecting a fall by a user wearing the fall detector, including: a trigger device configured to detect an trigger event identifying the time of a possible fall event in user data; a feature extractor configured to extract motion features from motion data and physiological features from physiological data from within a time window around the identified time location; and a machine learning classifier configured to determine whether the detected trigger event is a fall by the user based upon the at least one of the motion features and at least one of the physiological features.

Various embodiments are described, wherein the motion data includes one of acceleration data, height data, angular velocity data, and acceleration data and height data.

Various embodiments are described, further including an accelerometer configured to produce a portion of the motion data.

Various embodiments are described, further including on or more physiological sensors configured to produce the physiological data including one of heart rate data, skin conductance data, and heart rate and skin conductance data.

Various embodiments are described, wherein extracting motion features and physiological features further includes: determining a first physiological data value at a first time before the trigger event; determining a second physiological data value at the trigger event; determining a third physiological data value at a third time after the trigger event, wherein at least one physiological feature is based upon a difference between two of the first, second, and third physiological data values.

Various embodiments are described, wherein the physiological features are based upon a difference between the first and second physiological values, the second and third physiological values, the first and third physiological values, and second physiological value and one half the sum of the first and third physiological feature.

Various embodiments are described, wherein detecting an impact based upon motion data further includes determining that a change in acceleration over a specified time exceeds a threshold value.

Various embodiments are described, wherein the feature extractor is further configured to determine that extracted motion features are outside a specified normal range of values and then determining that the impact is not a fall by the user.

Various embodiments are described, further including an exception handler configured to receive an output from an exception machine learning classifier that indicates that the impact is not a fall, when a fall is indicated by the machine learning classifier.

Various embodiments are described, wherein the machine learning classifier includes: a motion classifier that determines whether the impact is a fall, a non-fall, or undetermined based upon the extracted motion features and a first threshold value and a second threshold value; and a physiological classifier that determines whether the impact is a fall or a non-fall based upon both the extracted motion features and the extracted physiological features when the output of the motion classifier is undetermined.

Various embodiments are described, further including a communication interface configured to receive the physiological data from a remote sensor.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1:
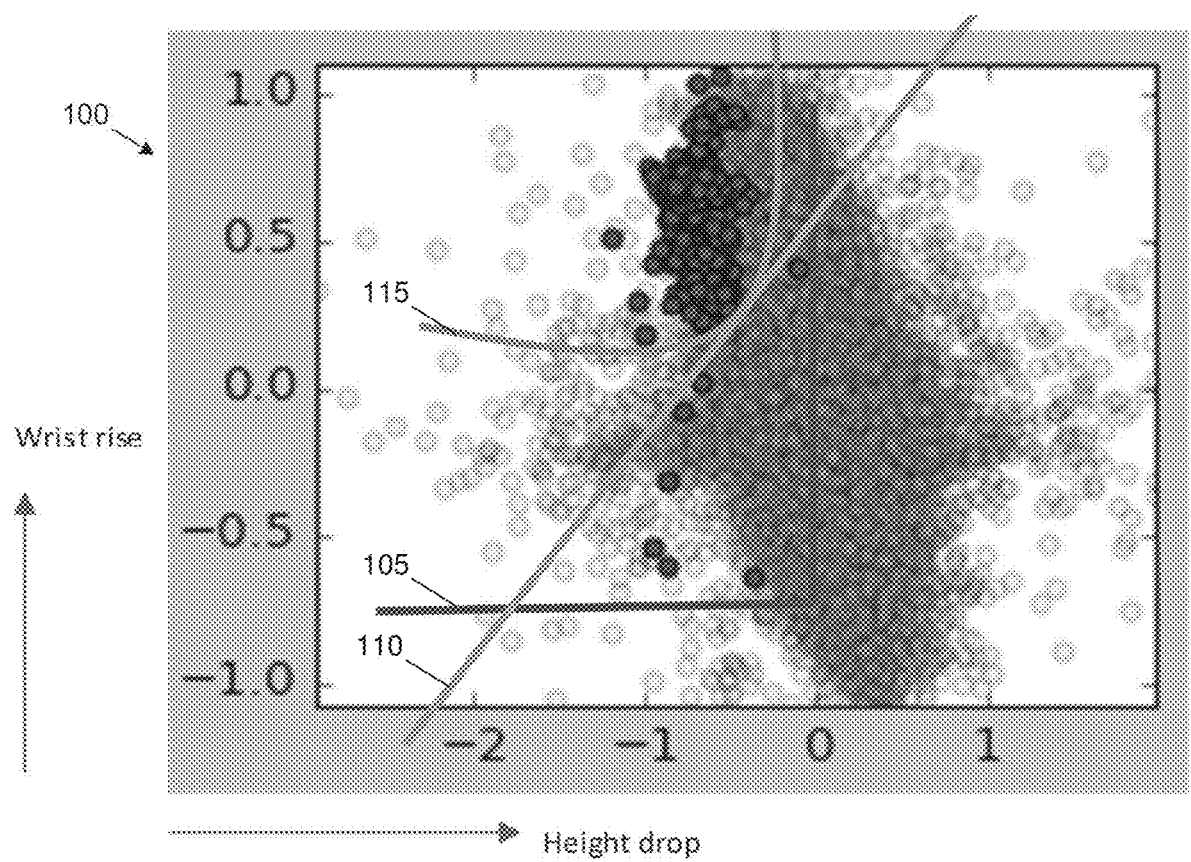
FIG. 1 illustrates a scatter plot of data points indicating fall/non-fall events with wrist rise and height drop as the features.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

When fall detection sensors are located on the torso of a user, the fall detection accuracy may be good. However, when the fall detector sensors are located elsewhere, for example at the wrist, it is more difficult to detect a fall as many normal movements by an arm may appear to be a fall. This is because there is more overlap between the various parameter values for the fall and non-fall situations. For example, height changes may happen due to wrist movements, without the body falling. As another example, this may also be true for orientation changes. Further, a wrist may hit some furniture or movements like hand waving and hand clapping may happen. These may appear to be impacts that are similar to a fall. Therefore, a need remains for improving the detection accuracy when differentiating between fall and non-fall events becomes difficult using various motion measurements. Current detection accuracies may require the user to regularly cancel false alarms that occur. This might be annoying to the user and may lead to a reduced adherence in wearing the device. The false alarms also burden the healthcare system by causing the workload of healthcare staff and costs of providing healthcare to increase.

Embodiments of a fall detection system are described herein that improve the detection accuracy of falls. The fall detection system is based on adding additional dimension(s) to the sensed feature space in order to improve the overall distinguishing power of the system. In addition to the mentioned physical characteristics of a fall, physiological measurements such as heart rate and skin conductivity may be used. It is known that the autonomous nervous system responds to stressful situations. For example, when a person encounters an unexpected situation and need to act quickly their heart rate and the skin conductivity will increase. This may happen at simple situations like food boiling over, or about missing to catch the train. As can be expected, it has been found this indeed also happens when a person falls unintentionally. Heart rate can be measured using various sensors such as a photoplethysmogram (PPG) or an electrocardiogram (ECG) sensor. The PPG sensor is an optical sensor that detects the change in blood volume near the sensor that is indicative of the user's pulse rate and hence (in general) heart rate. Accordingly, the PPG sensor can be placed at various locations on the body to determine a user's heart rate. The ECG sensor measures small electrical changes that indicate the beating of the user's heart. ECG sensors need to be placed near the heart in order to be effective. Further, skin conductivity may be measured via galvanic skin response. During non-fall events, these physiological values will not quickly increase in the same way as when a user falls.

Fall data was collected for a number of individuals known to have problems with frequent falls. In addition to typical motion related parameters, the individual's heart rate was also measured. It was observed that during and right after the fall occurs there is an increase in the individual's pulse rate. For example, the pulse rate may increase by order 10% over the pre-fall heart rate. Then fairly quickly, in say about 10 seconds, the individual's pulse rate tend to drop back to near its pre-fall value. This pattern in the change of the heart rate when an individual falls can be used to further determine if a fall has truly occurred, allowing for increased ability to differentiation fall and non-fall events. Another observation found that sometimes a fall was preceded by a lower than normal heart rate. Such a lower/reduced heart rate may be the, or contributing, cause of the individual's fall and is another parameter that may be used to assist in detecting falls.

Likewise, it has been observed that when an individual falls there is a spike in the individual's skin conductivity, which is typically due to increase sweating by the individual. After the fall, the skin conductivity does decrease back to near the pre-fall value, but it does more gradually than for example the heart rate.

The physiological features themselves do not provide distinguishing power regarding detecting falls. A change in heart rate or skin conductivity happens for many reasons and not only because of falls. Falls can still be detected, but at a low accuracy. However, by combining the physiological features with the physical features, the combined set of data leads to an improved discrimination between falls and non-falls because the additional data helps to separate the distributions of the falls and non-falls in the parameter space. In this way, the false alarm rate may be reduced, while maintaining a good detection sensitivity to actual falls.

Upon the occurrence of a trigger event, which will be further described below, the feature values may be computed such as the traditional motion related features like height change, impact, and orientation change, but in addition, physiological parameter(s) may be computed such as the heart rate and/or skin conductivity. More precisely, the heart rate may be determined shortly before the impact of the event (value_1), shortly after the fall (value_2), and a short time later (value_3). In one example the time of value_1 is 2-5 seconds before the impact, value_2 is about 5 seconds after the impact, and value_3 is about 10 seconds after the impact. Other times may be used as well. For example, the value at the impact can be used. Similar times may be used for skin conductance values, but value_3 may be longer than 10 seconds as the skin conductance value gradually returns to normal after a fall. These may be used to characterize the heart rate change as follows:

HR_change_1=value_2−value_1

HR_change_2_A=value_3−value_1

HR_change_2_B=value_2−value_3

HR_change_3=value_2−(value_1+value_3)/2

In another finding, people who fell had a heart rate that was lower than when they did not fall. So the absolute heart rate just before the fall may be used as well because of this finding because if the heart rate value just around the fall is low that might indicate a fall. Similar values may be calculated for skin conductance. These values along with the other motion features values are input into a classifier. Some or all of these physiological values or other modified versions in any combination may be used in the classifier. When including the physiologically related feature values, some of the motion related features may be discarded, or others can be added. The selected set is to be optimized for best classification accuracy. Correlations between the feature values influence which combination is optimal. A feature value that is highly correlated to another may not add much additional discriminating value, but can raise the total noise, and therefore it is better to select one of the two.

The classifier is a system known in the field of machine learning. The binary classifier is equivalent to a detector. A classifier takes as input a set of feature values and gives as an output the class or classes to which this set of features belong. This output may be in terms of a full membership (i.e., in or out the class) or as a partial membership value, such as a probability value. In the case of a binary classification, there are two classes (hence one being the complement of the other), and this type of classifier is equivalent to a detector. Detection theory stems from the field of signal processing.

Before the classifier is deployed, the classifier is trained: the classifier is presented with example sets of feature values that are labeled with the class they belong to. In the training procedure the current classifier iterates over the example sets. For each subsequent feature-value set, it computes the classification, which output is compared with the given labeling. The error that is determined from this comparison is used to adapt the classifier's internal parameters (or weights) such that the error is expected to be minimized based upon the adapted parameters. For example, in the case of neural networks, a typical optimization algorithm is gradient descent.

There are many forms of classifiers. Popular examples include support vector machines (SVM), decision tree, random forest, naive Bayesian classifier (NBC), neural networks including deep learning techniques, logistic regression, k-nearest neighbors (k-NN), etc.

One way to view a classifier is that it tries to find decision boundaries in the space spanned by the feature set. Every feature in the feature set is associated with a dimension in that space. So, a given example feature-value set (vector) constitutes a point in that space. The classifier partitions that space in subspaces, where each subspace associates with a class from the output. So, given a feature-value set, i.e., a point in the feature space, its class is determined from the subspace in which that feature point (vector) is located. During training, the boundaries between the subspaces are optimized for optimal classification.

In detection theory the typical case is to determine whether a signal is present in a continuously present noise background. A famous theorem, by Neyman and Pearson, states that for a given (chosen) false alarm rate, the most powerful test to decide whether the signal is present, is the likelihood ratio test (LRT). In the case of fall detection, the likelihood ratio equals $$LR = \frac{P(x \mid \text{Fall})}{P(x \mid nonFall)},$$

where P(x|Fall) is the likelihood the given feature values x are by a fall, and P(x|nonFall) is the likelihood the given feature values x are by a non-fall.

The LRT tests, for a given set x (i.e., observed/measured set of feature values), whether LR>θ, or not, where θ is the detection threshold configured by the designer of the fall detector. The NP-theorem states that for a given false alarm rate (=the number of falsely detected falls, i.e., in fact non-fall events) the detection sensitivity (=the fraction of actual falls that gets detected) is maximal. No other test can improve on that.

The NBC classifier implements the LRT, albeit with the (Naive) assumption that the feature values are independent of each other. Hence, the NBC classifier is a commonly used classifier.

FIG. 1 illustrates a scatter plot of data points indicating fall/non-fall events with wrist rise and height drop as the features. Only two features are used in this example to simplify the explanation and visualization of the classification process. The vertical axis plots the value of wrist rise (relative to the shoulder), and the horizontal axis plots the value of height drop of the patient. The darker circles illustrate examples of falls, and the lighter circles illustrate examples of non-falls. The lines depict different potential detection boundaries. The line 105 classifies everything with a wrist rise above −0.75 and a height drop less than 0 as a fall. As can be seen, no falls are missed, but also many false alarms will happen. The line 110 yields a better classifier while reducing the number of false alarms, at the expense of missing a few falls. The curved line 115 yields the best performance among these examples, by further reducing the number of false alarms. The training of the classifier seeks to set the detection boundary in an optimized way based upon the training data.

Figure 2:
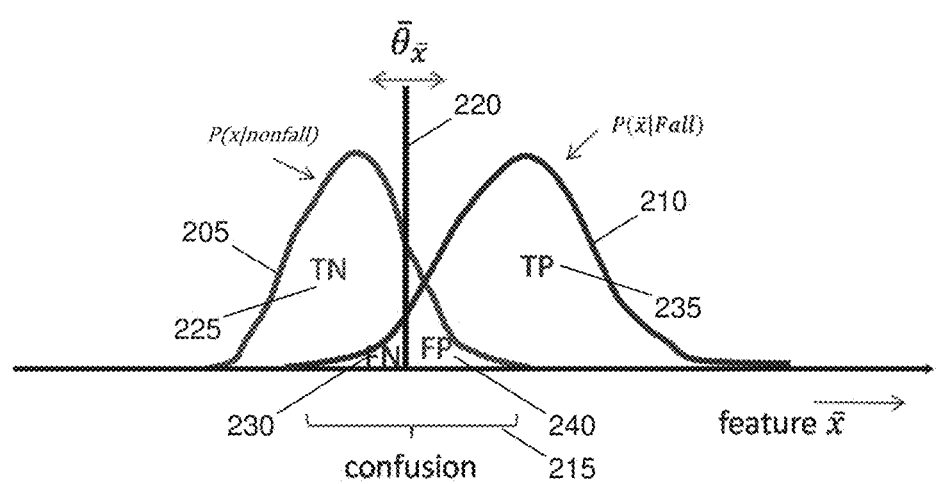
FIG. 2 illustrates another view of the data using a density distribution, i.e., how many events exhibit a certain feature value.

FIG. 2 illustrates another view of the data using a density distribution, i.e., how many events exhibit a certain feature value. For ease of visualization a 1-dimensional feature set is chosen, or, abstractly, the ordinate represents a vector.

The density curves P(x|Fall) 210 and P(x|nonFall) 205 are depicted, respectively. That is the likelihood of a fall/non-fall for each of the feature vectors x. The decision threshold 220 is also illustrated as a vertical line. This threshold 220 corresponds with the boundary plane in the feature space of FIG. 1. FIG. 2 also illustrates how detection performance can be evaluated: i.e., integrating the curves from left up to the threshold yields the false negative (FN) 230 percentage and the true negative (TN) 225 percentage, respectively; and integrating the curves from the threshold up to the right yields the true positive (TP) 235 percentage and false positive (FP) 240 percentage, respectively. As can be seen, there is a region of the features space 215 where confusion results because the two distributions overlap. Typically the threshold value 220 will fall in this area of confusion 215 and will result in some false negatives (i.e., actual falls being classified as non-falls) and some false positives (i.e., actual non-falls being classified as falls). As this threshold value varies there is a tradeoff between the probability of missed falls and the false alarm rate. When these distributions can be separated from one another to reduce the overlap, the performance of the classifier improves as the two different classes are more clearly distinguishable.

Figure 3:
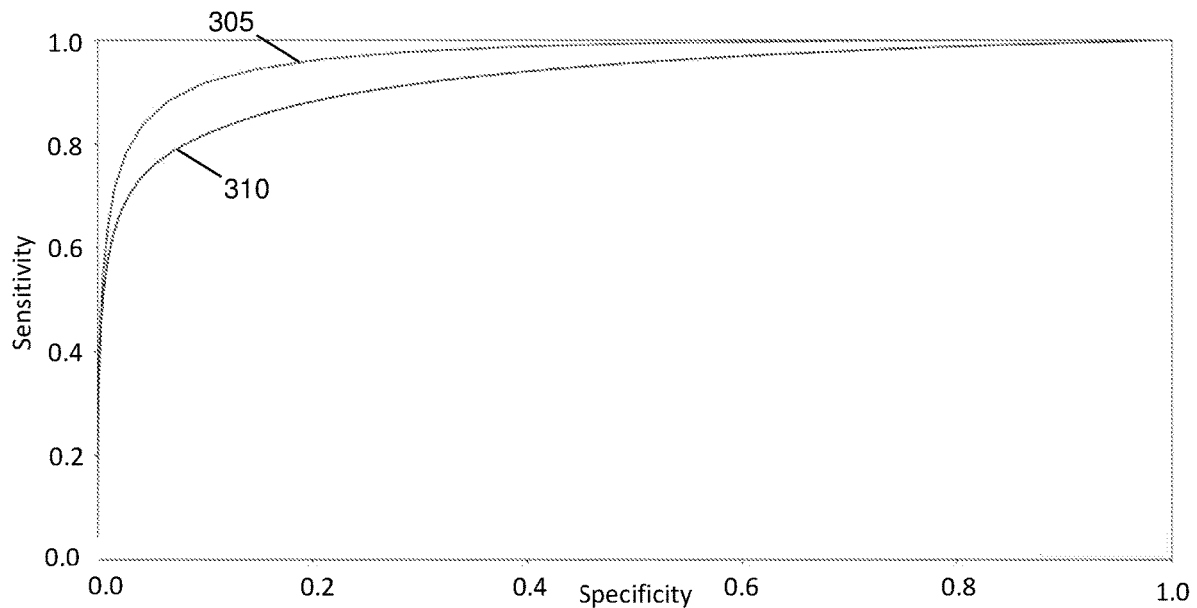
FIG. 3 illustrates a plot of ROC curves for a classifier using only motion data and a classifier using motion and physiological data.

When plotting the true positive rate (TPR=TP/(TP+FN)) on a vertical axis against the false positive rate (FPR=FP/(TN+FP)) on a horizontal axis the so-called receiver operating characteristics (ROC) curve results. The ideal ROC curve would follow the vertical axis and then follow the value of 1.0 for TPR across the plot. When the two distribution curves of FIG. 2 have less overlap, the ROC curve moves to left-upper corner (it always starts at (0,0) and ends at (1,1)). The overlap between the distributions may be reduced when either the two distributions (their means) move apart from each other or when the spread of the distribution curves reduces (the variance reduces), or when both of these happen. As previously stated, the distribution curve is to be understood to be the combined effect of all features in the selected set. FIG. 3 illustrates the plot of the ROC for a classifier using only motion data and a classifier using both motion data and physiological data. Specifically, in FIG. 3, the lower curve 310 is the performance of an example classifier using only the motion data. The upper curve 305 includes the use of heart rate information, and because this curve 305 is higher, it shows that the addition of the physiological information improves the performance of the classifier.

The addition of the physiological features (heart rate and/or skin conductivity), will cause the distributions of falls and non-falls to separate and/or sharpen, to result in better classifier performance. This was shown in the ROC curve of FIG. 3.

Figure 4:
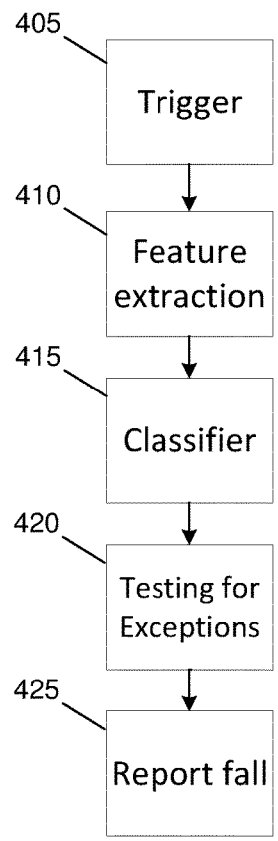
FIG. 4 illustrates the flow of the fall detection process carried out by the fall detector.

FIG. 4 illustrates the flow of the fall detection process carried out by the fall detector. The fall detector has a continuously running process, called trigger 405 that observes the motion signals for a possible fall. In another embodiment, the trigger 405 may look for a spike in the skin conductivity. Other events may be used as trigger events as well. The trigger may be implemented as a dedicated specific circuit, for example, using threshold signaling capabilities that state-of-the-art accelerometers provide or as software instructions running on a processor. For example, the accelerometer signals are processed to detect a potential impact. An impact may be determined when the acceleration measured by the accelerometer spikes above a threshold value, but other schemes are also conceivable, for example testing whether the energy in the acceleration signal passes a threshold, etc. The accelerometer signals may be sampled, for example, at a 50 Hz rate (but other rates may be used as well). As this process requires power that can drain the battery, the rate may be chosen based upon the fall detection performance and the device battery life. The trigger process 405 is designed to minimize the number of non-fall events while it will detect (pass) all possible falls, with the idea that the classifier will be able to further discriminate among falls and non-falls that are detected by the trigger 405. The role of the trigger is to minimize the number of calls to the classifier and by that save the power consumption.

Once the trigger 405 indicates an impact and a possible fall, the fall detector performs feature extraction 410. Various features may be extracted from the data collected around the time of the impact detected by the trigger process 405. Some motion feature values may include acceleration in three dimensions or these could be processed to produce the magnitude and a direction of the acceleration. Also changes in acceleration may be another feature that is extracted from the data. Further schemes to compute an impact value, changes in orientation, or height are other motion features that may be extracted from the motion data. In addition, physiological features such as changes in the heart rate or skin conductance as described above may be also calculated. In the heart rate example, the heart rate 3 seconds before the impact may be determined, and the heart rate at the impact, as well as 4.5 seconds and 10 seconds after the impact may be determined. Then one or more of the four heart rate change values described above or other features may be computed, for example, between the two values after the impact and between the value at impact and value at 10 sec after impact.

An optional feature of the feature extractor 410, may include detecting that a feature or data underlying the feature is outside of a normal range for a fall. This may be done, for example, by verifying that these values are within certain ranges. When the data is not within those ranges, it may indicate a non-fall or possibly a data error. When this occurs, the detected impact is ignored and not further processed. This may be considered a further refinement of the trigger 405 as the trigger 405 is intended to be low complexity that is run at a higher rate. This optional feature allows for reducing the need for running the classifier unnecessarily and will aid in extending the battery life of the fall detector.

Next, a classifier 415 receives the extracted features and makes a determination regarding whether a fall has occurred. The classifier 415 is optimized, but the classifier 415 will still classify a small percentage of real falls wrongly because the optimization process may set the decision boundaries within the distribution as explained in FIG. 1 and FIG. 2. As described above a variety of different types of machine learning classifiers may be used. Typically a NBC classifier may be used, but as discussed above a SVM, decision tree, random forest, neural networks including deep learning, logistic regression, k-NN, types of classifiers may also be used. In case of deep learning, the feature extraction step 410 might be integral part with the classifier 415, together constituting the (deep) network, as is known in the art. The classifier may be trained using a set of labeled data and a loss model. The training process proceeds to optimize the parameters of the classifier by adjusting the paraments of the classifier until the error or change in error reaches a certain threshold. Such models and training techniques are known in the art.

Optionally, the fall detector may also perform testing for exceptions 420 on the output of the classifier. For example, the classifier 415 may indicate that a fall has occurred, but the fall detector may also receive an indication that the user was, for example, walking or waving their hand at the time of the event classified as a fall. In such a case, the fall detection may be rejected and no fall is indicated. Such an approach may take advantage of other models that may be present in the fall detector. If for example the fall detector is a smart watch, the smart watch may have a machine learning model that detects that a user is walking or waiving their hand. These models may also be run on the data collected at the time of the suspected fall to determine, if in actuality other user behavior was occurring that was mis-classified as a fall. In other embodiments, these sorts of machine learning models may also be developed directly to be used with the fall detection classifier 415 to further improve the accuracy of the fall detector by excluding events that are indeed non-falls.

Finally, the fall detector may report 425 the fall. This report may go to an external system or person to alert others that the user has fallen and may need assistance. The fall detector may also provide a visual or audible alert to indicate to those near the user that the user has fallen so that the user may be assisted as needed. It also may provide a record of falls, either on the fall detector or on a remote device, for later use by healthcare providers. The fall report 425 may include an option for the user to cancel or revoke the fall alert.

In another embodiment, the classifier 415 may be a two stage classifier. In this approach, a first classifier is implemented that uses just the motion data and features. Outside of the area of confusion 215 (see FIG. 2), this type of first classifier may be very accurate. Accordingly, when a fall or non-fall classification is highly certain, then the output of the first classifier is the output of the classifier 415. This can be determined by the use of two thresholds. For example, when an event is below a first threshold it is clearly a non-fall. When an event is above a second threshold, it is clearly a fall. When the output of the first classifier is not certain, that is it is in between the two thresholds, then the classifier is undetermined. The output of the first classifier will be fall, non-fall, or undetermined. When the first classifier is undetermined then a second classifier using the physiological data may be used to further clarify the classification using the physiological features. This can improve the classification of events that are in the confusion area 215. The first classifier is trained using only motion data, and the second classifier is trained using both the motion data and the physiological data, possibly subset to those that have outcomes in the area of confusion. This approach may be used when the physiological data may be noisy or have other reliability or dropout issues. It avoids a mis-classification by a single classifier when the physiological data is problematic, but the motion data alone provides a clear and reliable classification based on only the motion data.

As discussed above, the heart rate may be measured using PPG or ECG sensors depending upon the location on the user's body and capability of the heart rate sensor in the fall detection device. Any current or future heart rate sensor that is compact and accurate enough may be used to provide the heart rate data for the fall detector. Likewise, any current of further skin conductivity sensor that is compact and accurate enough may be used to provide the skin conductivity data for the fall detection.

While the accuracy of motion only fall detection varies depending on where the motion sensors are on the users body, the incorporation of physiological data and features in the classification of falls can improve the accuracy of the fall detection no matter the location on the users body. Where the fall detector is on the wrist, arm, ankle, foot, or leg of the person that move much more than for example the torso of the user, the use of physiological data and features can greatly improve the accuracy of fall detection in such locations.

The fall detector can be implemented as a stand-alone device or be integrated into other user wearable devices such as a smart watch, fitness tracker, emergency alert device such as a pendant, etc. In any of these embodiments, the fall detector device would have motion sensors, such as accelerometers or atmospheric pressure sensors to provide the motion data for the classifier or be able to receive such data in a timely fashion from sensors located elsewhere on the users body. Further, these embodiments of the fall detector, would also include physiological sensors, such as heart rate sensor and/or skin conductivity sensors to provide the physiological data for the classifier or be able to receive such data in a timely fashion from sensors located elsewhere on the users body. For example, the user may use a smart watch with built in accelerometers, magnetometers, and atmospheric pressure sensors that provide the motion related data. Further, the user may wear a heart rate monitor strap across their chest to measure heart rate. The smart watch connects to the heart rate monitor wirelessly to collect the heart rate data for use in the classifier. Various other configurations of the sensors and processors to process the sensor data may also be used.

Figure 5:
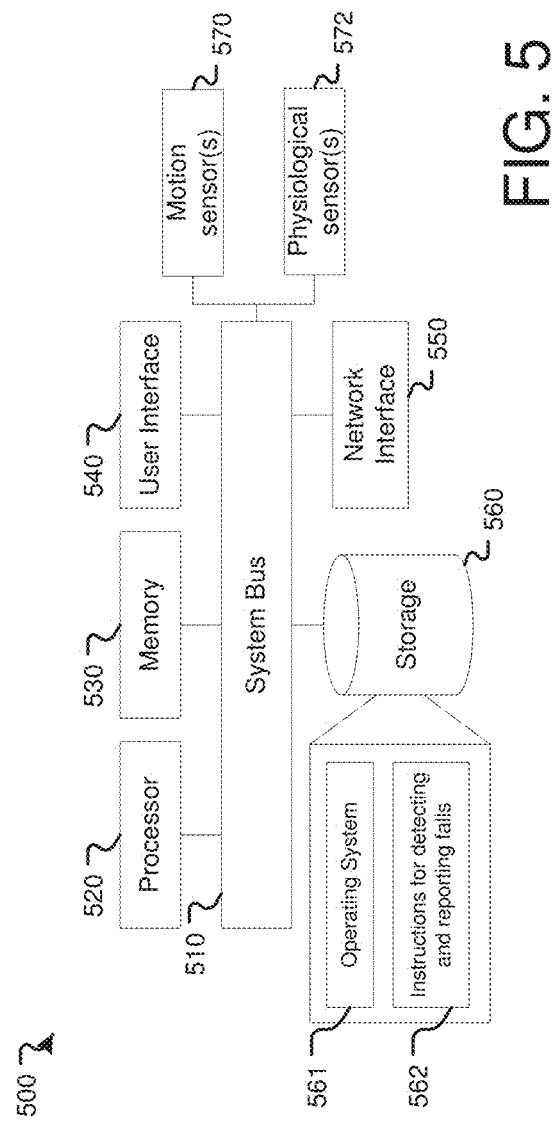
FIG. 5 illustrates an exemplary hardware diagram for the fall detector.

FIG. 5 illustrates an exemplary hardware diagram 500 for the fall detector. The hardware diagram 500 may implement the fall detection process described in FIG. 4 and indicate that a fall has occurred to another system or to a person connected to the user. As shown, the device 500 includes a processor 520, memory 530, user interface 540, network interface 550, storage 560, motion sensor(s) 570, and physiological sensor(s) 572 interconnected via one or more system buses 510. It will be understood that FIG. 5 constitutes, in some respects, an abstraction and that the actual organization of the components of the device 500 may be more complex than illustrated.

The processor 520 may be any hardware device capable of executing instructions stored in memory 530 or storage 560 or otherwise processing data. As such, the processor may include a microprocessor, a graphics processing unit (GPU), field programmable gate array (FPGA), application-specific integrated circuit (ASIC), any processor capable of parallel computing, or other similar devices. The processor may also be a special processor that implements machine learning models, in particular deep learning architectures.

The memory 530 may include various memories such as, for example L1, L2, or L3 cache or system memory. As such, the memory 530 may include static random-access memory (SRAM), dynamic RAM (DRAM), flash memory, read only memory (ROM), or other similar memory devices.

The user interface 540 may include one or more devices for enabling communication with a user and may present information to users. For example, the user interface 540 may include a display, a touch interface, a mouse, and/or a keyboard for receiving user commands. In some embodiments, the user interface 540 may include a command line interface or graphical user interface that may be presented to a remote terminal via the network interface 550.

The network interface 550 may include one or more devices for enabling communication with other hardware devices. For example, the network interface 550 may include a network interface card (NIC) configured to communicate according to the Ethernet protocol or other communications protocols, including wireless protocols. Additionally, the network interface 550 may implement a TCP/IP stack for communication according to the TCP/IP protocols. Various alternative or additional hardware or configurations for the network interface 550 will be apparent. The network interface 550 may be used to transmit a fall detection alert to a remote user or system. Also, where the motion sensor(s) 570 and/or the physiological sensor(s) 572 are separate from the fall detection device, the network interface 550 may facilitate receiving such data from the remote sensors.

The storage 560 may include one or more machine-readable storage media such as read-only memory (ROM), random-access memory (RAM), magnetic disk storage media, optical storage media, flash-memory devices, or similar storage media. In various embodiments, the storage 560 may store instructions for execution by the processor 520 or data upon which the processor 520 may operate. For example, the storage 560 may store a base operating system 561 for controlling various basic operations of the hardware 500. The storage 562 may store instructions for detecting and reporting falls.

It will be apparent that various information described as stored in the storage 560 may be additionally or alternatively stored in the memory 530. In this respect, the memory 530 may also be considered to constitute a "storage device" and the storage 560 may be considered a "memory." Various other arrangements will be apparent. Further, the memory 530 and storage 560 may both be considered to be "non-transitory machine-readable media." As used herein, the term "non-transitory" will be understood to exclude transitory signals but to include all forms of storage, including both volatile and non-volatile memories.

While the system 500 is shown as including one of each described component, the various components may be duplicated in various embodiments. For example, the processor 520 may include multiple microprocessors that are configured to independently execute the methods described herein or are configured to perform steps or subroutines of the methods described herein such that the multiple processors cooperate to achieve the functionality described herein. Such plurality of processors may be of the same or different types. Further, where the device 500 is implemented in a cloud computing system, the various hardware components may belong to separate physical systems. For example, the processor 520 may include a first processor in a first server and a second processor in a second server.

While FIG. 5 shows a system with a processor carrying out all of the functions of the fall detector, some of the functions of the fall detector may be implemented directly on hardware. For example, the trigger 405 may be implemented on dedicated hardware that is low power and tailored to detecting impact events. This may be implemented with a circuit designed to specially carry out this function or may include a low power processor that is programmed to carry out this function. Also, as the classifier is implemented using machine learning techniques, the classifier could be implemented using a circuit or processor optimized to carry out machine leaning functions.

The fall detection device described herein provides a technological improvement of current fall detection systems by using physiological data to improve the detection of falls. Because a fall will quickly produce a physiological reaction in the person who falls, this may be used to improve the detection of falls. This is especially beneficial, when the fall detection device is worn on an area of the body where other normal motion may lead to false fall detection alerts.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for detecting a fall by a user wearing a fall detector, comprising:
   detecting a trigger event identifying the time location of a possible fall event in user data;
   extracting motion features from motion data and physiological features from physiological data from within a time window around the identified time location; and
   determining whether the detected trigger event is a fall by the user by inputting the at least one of the motion features and at least one of the physiological features into a machine learning classifier that has been trained to optimize parameters of the classifier by adjusting the parameters until a measure of erroneous fall determination reaches a certain threshold.

2. The method of claim 1, wherein the motion data includes one of acceleration data, height data, angular velocity data, and acceleration data and height data.

3. The method of claim 1, wherein the motion data includes data from an accelerometer.

4. The method of claim 1, wherein the physiological data include one of heart rate data, skin conductance data, and heart rate and skin conductance data.

5. The method of claim 1, wherein extracting motion features and physiological features further comprises:
   determining a first physiological data value at a first time before the trigger event;
   determining a second physiological data value at the trigger event;

determining a third physiological data value at a third time after the trigger event,
wherein at least one physiological feature is based upon a difference between two of the first, second, and third physiological data values.

6. The method of claim 5, wherein the physiological features are based upon a difference between the first and second physiological values, the second and third physiological values, the first and third physiological values, and second physiological value and one half the sum of the first and third physiological feature.

7. The method of claim 1, wherein detecting an impact based upon motion data further comprises determining that a change in acceleration over a specified time exceeds a threshold value.

8. The method of claim 1, further comprising determining that extracted motion features are outside a specified normal range of values and then determining that the impact is not a fall by the user.

9. The method of claim 1, further comprising when a fall is indicated, receiving an output from an exception machine learning classifier that indicates that the impact is not a fall.

10. The method of claim 1, wherein the machine learning classifier includes:
a motion classifier that determines whether the impact is a fall, a non-fall, or undetermined based upon the extracted motion features and a first threshold value and a second threshold value; and
a physiological classifier that determines whether the impact is a fall or a non-fall based upon both the extracted motion features and the extracted physiological features when the output of the motion classifier is undetermined.

11. The method of claim 1, further comprising receiving the physiological data from a remote sensor.

12. A fall detector for detecting a fall by a user wearing the fall detector, comprising:
a trigger device configured to detect a trigger event identifying the time of a possible fall event in user data;
a feature extractor configured to extract motion features from motion data and physiological features from physiological data from within a time window around the identified time location; and
a machine learning classifier configured to determine whether the detected trigger event is a fall by the user based upon the at least one of the motion features and at least one of the physiological features.

13. The device of claim 12, wherein the motion data includes one of acceleration data, height data, angular velocity data, and acceleration data and height data.

14. The device of claim 12, further comprising an accelerometer configured to produce a portion of the motion data.

15. The device of claim 12, further comprising on or more physiological sensors configured to produce the physiological data including one of heart rate data, skin conductance data, and heart rate and skin conductance data.

16. The device of claim 12,
wherein extracting motion features and physiological features further comprises:
determining a first physiological data value at a first time before the trigger event;
determining a second physiological data value at the trigger event;
determining a third physiological data value at a third time after the trigger event,
wherein at least one physiological feature is based upon a difference between two of the first, second, and third physiological data values.

17. The device of claim 16, wherein the physiological features are based upon a difference between the first and second physiological values, the second and third physiological values, the first and third physiological values, and second physiological value and one half the sum of the first and third physiological feature.

18. The device of claim 12, wherein detecting an impact based upon motion data further comprises determining that a change in acceleration over a specified time exceeds a threshold value.

19. The device of claim 12, wherein the feature extractor is further configured to determine that extracted motion features are outside a specified normal range of values and then determining that the impact is not a fall by the user.

20. The device of claim 12, further comprising an exception handler configured to receive an output from an exception machine learning classifier that indicates that the impact is not a fall, when a fall is indicated by the machine learning classifier.

21. The device of claim 12,
wherein the machine learning classifier includes:
a motion classifier that determines whether the impact is a fall, a non-fall, or undetermined based upon the extracted motion features and a first threshold value and a second threshold value; and
a physiological classifier that determines whether the impact is a fall or a non-fall based upon both the extracted motion features and the extracted physiological features when the output of the motion classifier is undetermined.

22. The device of claim 12, further comprising a communication interface configured to receive the physiological data from a remote sensor.

* * * * *